United States Patent [19]
Claussen et al.

[11] 3,965,094
[45] June 22, 1976

[54] PROCESS FOR THE MANUFACTURE OF 2-ARYL-V-TRIAZOLE

[75] Inventors: Uwe Claussen, Leverkusen; Heinrich Gold, Schildgen; Josef Schroeder, Cologne, all of Germany

[73] Assignee: Bayer Aktiengesellschaft, Leverkusen, Germany

[22] Filed: Mar. 2, 1973

[21] Appl. No.: 337,559

[30] Foreign Application Priority Data
Mar. 3, 1972 Germany............................ 2210261

[52] U.S. Cl...................... 260/240 C; 260/288 CE; 260/296 R; 260/308 A; 260/343.2 R
[51] Int. Cl.$^2$................ C07D 249/06; C07D 405/04
[58] Field of Search..................... 260/308 A, 240 C
[56] References Cited
UNITED STATES PATENTS
3,666,758   5/1972   Dorlars et al.................. 260/308 A OTHER PUBLICATIONS
Wagner et al., Synthetic Organic Chemistry, (New York, 1953), pp. 645–647.

*Primary Examiner*—Raymond V. Rush
*Attorney, Agent, or Firm*—Plumley and Tyner

[57] ABSTRACT

2-Aryl-v-triazoles are obtained by reacting α-oximinoaryl-hydrazones of the formula

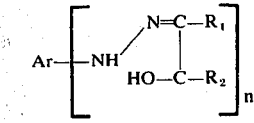

in which Ar represents an aromatic-carbocyclic or aromatic-heterocyclic radical, $R_1$ denotes alkyl, aryl or nitro, $R_2$ denotes hydrogen, alkyl or aryl and $n$ denotes the numbers 1 or 2 with at least 2 equivalents of an isocyanate or carbamic acid halide or with at least 1 equivalent of a pyrocarbonic acid ester.

7 Claims, No Drawings

PROCESS FOR THE MANUFACTURE OF 2-ARYL-V-TRIAZOLE

A relatively comprehensive literature already exists on the synthesis of 2-aryl-v-triazoles.

Thus, for example, Chem. Reviews 46, 1 – 68 (1950) describes a process in which v-triazoles are manufactured by thermal treatment of α-acyloximinohydrazones. However, yields of only maximally 50% are achievable by this method.

On the other hand, the process known from German Pat. No. 1,168,437 suffers from the disadvantage that, whilst giving moderate yields, it is not generally applicable in that it only leads to triazoles containing nitro groups.

Whilst, according to the process described in British patent specification No. 1,215,507, in which α-oximinoarylhydrazones or their O-acyl compounds are subjected to a cyclising condensation in a urea melt at relatively high temperatures, yields of 70 to 85% are achievable when working carefully on a laboratory scale, these yields drop considerably, especially in the case of compounds containing sulpho groups, that is to say water-soluble compounds, if attempts are made to carry out this method on a large industrial scale.

A further disadvantage of this process is that the large amounts of ammonia waste gases, containing hydrocyanic acid, which are at the same time produced must be trapped in expensive absorption installations.

It has now been found that 2-aryl-v-triazoles are obtained in almost quantitative yields, and whilst avoiding the abovementioned disadvantages, if α-oximinoarylhydrazones of the general formula

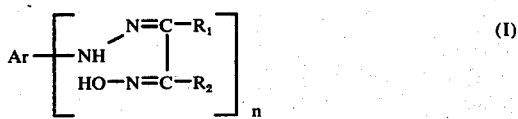

in which
Ar represents an aromatic-carbocyclic or aromatic-heterocyclic radical,
$R_1$ denotes alkyl, aryl or nitro,
$R_2$ denotes hydrogen, alkyl or aryl and
n denotes the numbers 1 or 2
are reacted with at least 2 equivalents of an isocyanate or carbamic acid halide or with at least 1 equivalent of a pyrocarbonic acid ester, preferably in the presence of a solvent.

In comparison to the previously known triazole cyclisations, the process according to the invention is carried out at relatively low temperatures, namely between 20°C and 100°C. Preferably, however, the isocyanate variant is carried out at 60° – 80°C and the pyrocarbonic acid ester variant at 30° – 40°C.

Though the process according to the invention can in principle be carried out without the use of a solvent, it is nevertheless advisable to carry out the exothermic reaction in the presence of water or of a suitable organic solvent. Equally, the use of a base catalyst (approx. 0.05 – 0.1% by weight relative to the amount of (I) employed) is frequently of advantage. Suitable catalysts are alkali metal hydroxides, alkali metal carbonates, pyridine, quinoline, dimethylaniline and others. Suitable solvents for the isocyanate or carbamic acid halide variant are especially polar ones. Examples are formamide, dimethylformamide, dimethylacetamide, N-methylpyrrolidone, ε-caprolactam, pyridine, picolines, quinoline, triethylamine, dimethylsulphoxide and water/alcohol mixtures. If α-oximinoarylhydrazones of the formula (I) which are free of groups which confer solubility in water are used as the starting material it is additionally possible to employ less polar solvents, such as hydrocarbons, ethers, halogenated hydrocarbons, ketones and the like. As examples there may be mentioned: xylene, chlorobenzene, dichlorobenzene, glycol monomethyl ether and cyclohexanone.

In addition to pure water, suitable solvents for the pyrocarbonic acid ester variant are above all alcohol/water mixtures, lower aliphatic alcohols and ketones as well as dimethylformamide, pyridine and dimethylsulphoxide.

The α-oximinohydrazones of the formula (I) required for the process according to the invention are largely known (compare British patent specification No. 1,215,507) or can be manufactured in a manner which is in itself known, for example by condensation of appropriate arylhydrazines with α-oximinoketones of the formula

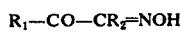

wherein $R_1$ and $R_2$ have the initially mentioned meaning.

Suitable α-oximinoarylhydrazones of the formula (I) are especially those in which Ar, $R_1$ and $R_2$ have the following meaning:

Ar: radicals of the benzene, naphthalene, diphenyl, diphenylmethyl, diphenylethane, stilbene, tolane, pyridine, triazole, imidazole, pyrazole, coumarine or carbostyrile series which optionally contain further substituents, such as alkyl, alkoxy, halogen, OH, CN, COOH, $CONH_2$, $SO_3H$, alkylcarbonyl, alkoxycarbonyl, alkylsulphonyl, phenylsulphonyl and tolylsulphonyl, with alkyl and alkoxy preferably being understood as radicals with 1 – 4 C atoms.

$R_1$: $C_1$–$C_4$-alkyl radicals which can optionally be further substituted by halogen atoms, OH, COOH or $C_1$–$C_4$-alkoxy, and phenyl radicals which are optionally substituted by halogen, $C_1$–$C_4$-alkyl or $C_1$–$C_4$-alkoxy.

$R_2$: hydrogen and the alkyl and aryl radicals mentioned under $R_1$.

Suitable isocyanates for the cyclisation, according to the invention, of the α-oximinoarylhydrazones (I) are those of the formula

in which Q denotes hydrogen, $C_1$–$C_6$-alkyl, $C_5$–$C_7$-cycloalkyl, (optionally substituted by halogen, $C_1$–$C_4$-alkyl, $C_1$–$C_4$-alkoxy or nitro) phenyl or phenylcarbonyl or phenylsulphonyl.

As examples there may be mentioned: HNCO, methylisocyanate, ethylisocyanate, methoxymethylisocyanate, cyclohexylisocyanate, phenylisocyanate, tolylisocyanate, nitrophenylisocyanate, benzoylisocyanate, phenylsulphonylisocyanate and toluylenediisocyanate.

Suitable carbonimide acid halides for the reaction according to he invention are those of the formula

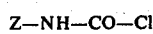

wherein Z represents a $C_1$–$C_6$-alkyl, phenyl, tolyl, anisoyl or chlorophenyl radical.

Suitable pyrocarbonic acid esters are especially pyrocarbonic acid methyl ester or ethyl ester.

In carrying out in practice the isocyanate or carbamic acid variant of the process according to the invention, an appropriate procedure is to dissolve or suspend the α-oximinoarylhydrazones of the formula (I) in a twofold to 10-fold amount of the abovementioned solvents and adding at least 2 equivalents of an isocyanate or carboxylic acid halide dropwise, whilst stirring, in such a way that the reaction temperature remains below the boiling point of the solvent. After the evolution of carbon dioxide has ended, the reaction mixture is worked up in the usual manner. The working up proves particularly simple when using compounds of the formula (I) which are water-soluble, that is to say which contain sulpho groups, in that the reaction mixture is introduced into water, the insoluble substituted urea arising as a by-product is filtered off and the reaction product is salted out from the filtrate.

The pyrocarbonic acid ester variant is even more economical since herein only easily volatile, that is to say readily separable, compounds — namely carbon dioxide and alcohol — are produced as by-products.

The 2-aryl-v-triazoles obtainable according to the process of the invention, which correspond to the formula

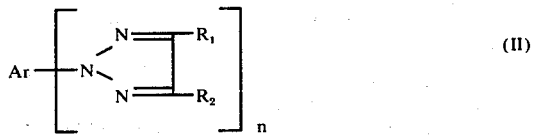

in which Ar, $R_1$, $R_2$ and n have the abovementioned meaning are very largely known and represent valuable optical brighteners, UV-absorbers as well as brightener intermediate products and dyestuff intermediate products.

Thus, for example, compounds of the formula (II) in which Ar represents a stilbene, coumarine, naphthalimide and dibenzothiophenedioxy radical, are excellent optical brighteners (see British Pat. Nos. 1,108,416, 1,155,229, 1,154,995, 1,113,918 and 1,201,759 and U.S. Pat. No. 3,459,744).

Those compounds in which Ar represents a p-tolyl radical ($n = 1$) or diphenylethane radical ($n = 2$) can be converted in accordance with known processes into stilbene brighteners (see, for example, U.S. Pat. No. 3,351,592 and French Pat. No. 1,480,699).

Aryltriazoles of the formula (II) which contain nitro groups can be converted in accordance with known processes into corresponding aminoaryltriazoles which represent valuable starting materials for the manufacture of azo dyestuffs (see French Pat. No. 1,391,676 and 1,398,366).

2-Phenyl-4-methyl-v-triazole is an effective UV-absorber (Chem. Abstr. 57, 8100 d).

The process according to the invention will be explained in more detail with the aid of the following examples.

EXAMPLE 1

706 g of the disodium salt of 4,4′-bis-(α-oximinoaceto-phenone-hydrazono)-diphenylethane-2,2-disulphonic acid according to Example 2 of British patent specification No. 1,215.507 are suspended in 3,000 ml of dimethylformamide (DMF). 500 g of phenylisocyanate are added dropwise over the course of 1 hour to the solution obtained by warming to 75°C. During the exothermic reaction, 45 liters of carbon dioxide are evolved. The reaction mixture is stirred for a further 30 minutes and then stirred into 20 liters of water at 70°C and the diphenylurea which hereupon crystallises out is filtered off and washed with 1 liter of water at 70°C. The filtrate is treated with 2.6 kg of sodium chloride at 70°C and the reaction product which precipitates is filtered off hot and is washed 3 times with 1 liter at a time of 15% strength hot sodium chloride solution. After drying, 920 g of crude product containing 73.5% of pure cyclisation product of the formula

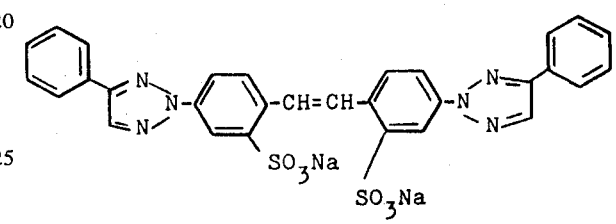

are obtained, corresponding to a yield of 96.5%. Similarly good results are obtained if instead of the 3,000 ml of DMF the same amount of pyridine or N-methylpyrrolidone is used. If water is used as the reaction medium, it is advisable to employ a larger excess of phenylisocyanate (a total of approx. 600 g).

EXAMPLE 2

706 g of the α-oximinoarylhydrazone employed in Example 1 are dissolved in 2,500 ml of dimethylformamide and 260 g of sodium cyanate dissolved in 1,500 ml of water are added. A little silicone anti-foaming agent is added and 1,460 g of 10% strength aqueous hydrochloric acid are slowly added dropwise at 80° – 85°C, it being desirable for the stem of the dropping funnel to dip into the solution. When 46 l of $CO_2$ have been evolved, the mixture is stirred for a further 30 minutes and the product is salted out hot, filtered off and washed with 3% strength hot aqueous sodium chloride solution until the filtrate issues clear. After recrystallisation of the crude 4,4′-bis-[4-phenyl-triazolyl-(2)]-stilbene-2,2′-disulphonic acid from aqueous alcohol, 470 g (71% of theory) of pure product are obtained.

EXAMPLE 3

14.4 g of N-(p-nitrophenyl)-α-oximinoacetophenonehydrazone are dissolved in 200 ml of dimethylformamide and 14 g of phenylisocyanate are added in the presence of a pinch of potassium carbonate. Vigorous evolution of $CO_2$ starts at about 50°C and when it has ceased the solution is stirred for a further 30 minutes and poured into water and the crystals which have precipitated are filtered off. After drying, 33 g of crude product are obtained and are extracted by boiling with 150 ml of toluene. 13.0 g (94% of theory) of pale yellow crystals of the formula

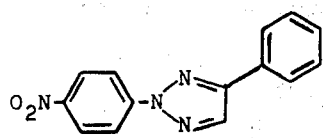

of melting point 184°–186°C crystallise from the filtrate.

EXAMPLE 4

41.2 g of N-(3-phenyl-coumarinyl-7)-α-oximino-propio-phenone-hydrazone (95.8% pure material) are dissolved in 400 ml of DMF at room temperature and 13 g of phenylisocyanate are added dropwise at 40° – 50°C. After a short time, a light yellow precipitate is formed, which, after 30 minutes stirring, is completely precipitated by adding an equal volume of methanol and is filtered off and washed with methanol. 49 g (83% of theory) of the carbamic acid ester of the formula

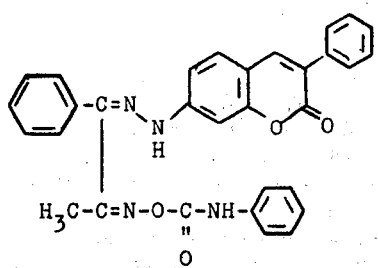

are obtained; this product melts, as the DMF-complex (yellow crystals which rapidly turn dark in light) at 143°–145°C, and can be cyclised, by the action of a further mol of phenylisocyanate, to give the corresponding 7-triazolylcoumarine (compare next example).

EXAMPLE 5

385 g of α-oximinoarylhydrazone from 7-hydrazino-3-phenylcoumarine and oximinopropiophenone are dissolved in 1,500 ml of pyridine and 260 g of phenylisocyanate are added rapidly at 75° – 80°. In the course thereof, the temperature rises to 90°C. 2 minutes after starting to add the phenylisocyanate to the solution of the α-oximinohydrazone a vigorous evolution of carbon dioxide starts, which is proportional to the amount of isocyanate added. After the addition of the isocyanate, the mixture is further stirred until the temperature has dropped to 65°C and 2,000 ml of methanol are added, whereupon the cyclisation product precipitates. It is filtered off after cooling to 10°C and washed once on the filter with cold methanol.

After drying, 300 g of the cyclisation product of the formula

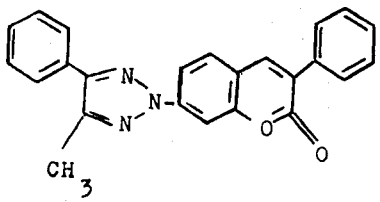

are obtained (yield: 86.5%). After crystallisation from glycol monomethyl ether, pale yellow analytically pure crystals which melt at 161°C are isolated.

EXAMPLE 6

67.4 g of hydrazone from 2 mols of oximinoacetophenone and 1 mol of 4,4'-dihydrazinostilbene-2,2-disulphonic acid are stirred into 200 ml of dimethylformamide and the suspension is treated dropwise with 35 g of pyrocarbonic acid diethyl ester whilst stirring. The exothermic reaction, with evolution of carbon dioxide, already commences after a short time. The reaction is maintained at 45° – 50°. In total, 10 liters of carbon dioxide are evolved. Finally the solution, which has in the meantime become clear, is additionally kept for 30 minutes at 110° in the course of which only little additional carbon dioxide is evolved, and the reaction solution is then stirred into 800 ml of sodium chloride solution which contains 60 ml of 10% strength sodium hydroxide solution. The product which has precipitated is filtered off and washed with sodium chloride solution and then with cold water. The press cake is stirred into 2.8 liters of water at 90°, 20 ml of 10% strength sodium hydroxide solution are added and sodium hypochlorite solution is added dropwise to the almost clear solution at 85° – 90°C until the blue colouration on potassium iodide/starch paper persists. 10 g of sodium dithionite and 120 g of sodium chloride are now added. The product which has precipitated is filtered off hot and washed with sodium chloride solution and then with cold water. After drying, 65 g of a yellow powder consisting to the extent of 90% (hence corresponding to a yield of 87%) of the compound of the formula

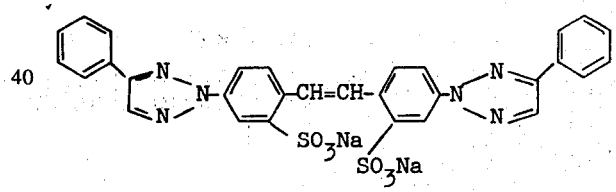

is obtained. Recrystallisation from alcohol/water (1:1) yields an analytically pure light yellow preparation which possesses the same spectroscopic properties as a preparation in the literature (compare, for example, British patent specification No. 1,215,507).

EXAMPLE 7

39.7 g of hydrazone from 3-phenyl-7-hydrazinocoumarine and α-oximinopropiophenone are suspended in 200 ml of dimethylformamide and the suspension is warmed to 45°–50°C. 20 g of pyrocarbonic acid diethyl ester are added dropwise to the suspension, whereupon a reaction occurs, which manifests itself through a vigorous evolution of $CO_2$. In the course of 30 minutes, 4.7 l of $CO_2$ are evolved, measured by gas-volumetric methods. Towards the end of the evolution of gas, the suspension dissolves to give a dark solution, the temperature of which is then about 55°. The mixture is stirred for a further 10 minutes, 30 ml of hot water (50°) are added and the whole is stirred until cold. The crystallisation of the crude 3-phenyl-7[2(2-phenyl-5-methyl)-1,2,3-triazolyl]-coumarine, which takes places from approx. 25° onwards, is completed by placing the mixture in ice. The product is filtered off and rinsed with 20 ml of methanol, and after drying 38.5 g of yellow crystals are obtained, in which the spectroscopically determined content of 3-phenyl-7-[2-(4-phenyl-5-methyl)-1,2,3-triazolyl]-coumarine is 82.5%. After recrystallisation from pyridine/water, an analytically pure light yellow product of melting point 163° – 164°C is obtained.

EXAMPLE 8

21 g (0.1 mol) of nitroglyoxaloxime-phenylhydrazone are dissolved in 100 ml of DMF in the presence of a pinch of potassium carbonate at 60°C and 13 g of phenylisocyanate are added. An exothermic reaction, with evolution of $CO_2$ (2.4 l) occurs. The solution is stirred for a further 20 minutes and diluted with 150 ml of water, and the crystal paste which has precipitated is separated off, dried and extracted by boiling with 100 ml of toluene, whereupon the diphenylurea is left undissolved. After filtering, and washing the residue with 10 ml of hot toluene, the filtrate yields 17.2 g (= 91% of theory) of a product of the formula

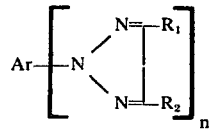

in the form of yellow crystals which melt at 122°–123°C.

We claim:

1. In the process of preparing a 2-aryl-1,2,3-triazole of the formula

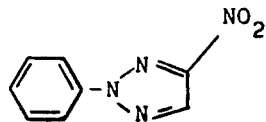

by heating an α-oximino hydrazone of the formula

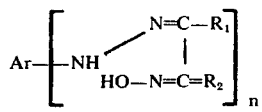

in which

Ar is an aromatic-carbocyclic or aromatic-heterocyclic radical;

$R_1$ is $C_1$–$C_4$-alkyl; $C_1$–$C_4$-alkyl substituted by halogen, OH, COOH or $C_1$–$C_4$-alkoxy; phenyl; or phenyl substituted by halogen, $C_1$–$C_4$-alkyl or $C_1$–$C_4$-alkoxy; and $R_2$ is hydrogen or $R_1$; and n is the number 1 or 2;

the improvement comprising carrying out the reaction in the presence of at least 2 equivalents of $$Q - NCO \text{ or } Z - NH - COCl$$

in which

Q is hydrogen; $C_1$–$C_6$-alkyl; $C_5$–$C_7$-cycloalkyl; phenyl; phenyl substituted by halogen, $C_1$–$C_4$-alkyl, $C_1$–$C_4$-alkoxy or nitro; phenylcarbonyl or phenylsulphonyl; and Z is $C_1$14 $C_6$-alkyl, phenyl, tolyl, or chlorophenyl; or in the presence of at least 1 equivalent of pyrocarbonic acid methyl or ethyl ester.

2. The process of claim 1 conducted in the presence of a basic catalyst selected from the group consisting of alkali metal hydroxides, alkali metal carbonates, pyridine, quinoline and dimethylaniline.

3. The process of claim 1 in which the reaction is carried out in the presence of at least 2 equivalents of Q-NCO.

4. The process of claim 1 in which the reaction is carried out in the presence of a solvent as an additional ingredient.

5. The process of claim 4 in which the solvent is water or a water/alcohol mixture.

6. The process of claim 4 in which the solvent is dimethylformamide.

7. The process of claim 1 in which the reaction is conducted between 20°C and 100°C.

* * * * *

UNITED STATES PATENT OFFICE
CERTIFICATE OF CORRECTION

PATENT NO. : 3,965,094

DATED : June 22, 1976

INVENTOR(S) : Uwe Claussen et al

It is certified that error appears in the above-identified patent and that said Letters Patent are hereby corrected as shown below:

In Claim 1, Column 8, line 27,
"Z is $C_1$14 $C_6$-alkyl, should be ---Z is $C_1$-$C_6$-alkyl,---.

Signed and Sealed this

Thirty-first Day of May 1977

[SEAL]

Attest:

RUTH C. MASON
*Attesting Officer*

C. MARSHALL DANN
*Commissioner of Patents and Trademarks*